US012575725B2

(12) United States Patent
Ungerstedt

(10) Patent No.: US 12,575,725 B2
(45) Date of Patent: Mar. 17, 2026

(54) PROCTOSCOPE

(71) Applicant: Developeration AB, Enskede (SE)

(72) Inventor: Johan Ungerstedt, Enskede (SE)

(73) Assignee: Developeration AB, Enskede (SE)

( * ) Notice: Subject to any disclaimer, the term of this patent is extended or adjusted under 35 U.S.C. 154(b) by 270 days.

(21) Appl. No.: 18/274,816

(22) PCT Filed: Feb. 4, 2022

(86) PCT No.: PCT/EP2022/052760
§ 371 (c)(1),
(2) Date: Jul. 28, 2023

(87) PCT Pub. No.: WO2022/167606
PCT Pub. Date: Aug. 11, 2022

(65) Prior Publication Data
US 2024/0115124 A1      Apr. 11, 2024

(30) Foreign Application Priority Data

Feb. 4, 2021      (EP) ..................................... 21155308

(51) Int. Cl.
*A61B 1/31* (2006.01)
*A61B 1/00* (2006.01)
(Continued)

(52) U.S. Cl.
CPC ............ *A61B 1/31* (2013.01); *A61B 1/00105* (2013.01); *A61B 1/00147* (2013.01); *A61B 1/06* (2013.01);
(Continued)

(58) Field of Classification Search
None
See application file for complete search history.

(56) References Cited

U.S. PATENT DOCUMENTS 348,843 A * 9/1886 Hamilton ................. A61B 1/31
600/184
2,672,859 A * 3/1954 Jones ....................... A61B 1/32
604/106
(Continued)

FOREIGN PATENT DOCUMENTS

CN      110123256 A      8/2019
CN      111990962 A * 11/2020 ............. A61B 17/42
(Continued)

OTHER PUBLICATIONS

Brazilian Office Action from Corresponding Brazilian Patent Application No. 112023014901-0, dated Mar. 31, 2025.
(Continued)

*Primary Examiner* — Jan Christopher L Merene
(74) *Attorney, Agent, or Firm* — Ronald M. Kachmarik; Cooper Legal Group LLC

(57)      ABSTRACT

A proctoscope including a body, a handle extending therefrom and an elongated element, extended along an axis, with forward and aft ends and. The aft end attached to the body and open for interior access. At least one opening and/or a transparent section in the elongated element. A reference marking along the opening/transparent section and readable via the open aft end. A positioning device, to support at a treatment area, that includes an elongated position adjustment device, with a forward end contact surface, that is movably arranged substantially parallel to the axis and that extends from the body in the same direction as the elongated element from the body. Locking means arranged to secure the elongated position adjustment device in a selected position. The forward end contact surface to bear against the skin of a patient to maintain and support a position along the longitudinal axis at the treatment area.

10 Claims, 8 Drawing Sheets

(51) Int. Cl.
   *A61B 1/06*          (2006.01)
   *A61B 1/32*          (2006.01)
   *A61B 90/00*         (2016.01)

(52) U.S. Cl.
   CPC ............ *A61B 1/32* (2013.01); *A61B 1/00066*
         (2013.01); *A61B 2090/036* (2016.02); *A61B*
                               *2090/0807* (2016.02)

(56)                References Cited

U.S. PATENT DOCUMENTS

| | | | | |
|---|---|---|---|---|
| 5,137,520 | A * | 8/1992 | Maxson | A61M 25/02 |
| | | | | 128/DIG. 26 |
| 6,142,931 | A * | 11/2000 | Kaji | A61B 17/3421 |
| | | | | 600/105 |
| 8,475,362 | B2 * | 7/2013 | Sohn | A61B 1/00147 |
| | | | | 600/137 |
| 11,547,292 | B2 * | 1/2023 | Miller | A61B 1/0676 |
| 2002/0147385 | A1 * | 10/2002 | Butler | A61B 1/00137 |
| | | | | 600/114 |
| 2005/0228371 | A1 | 10/2005 | West et al. | |
| 2010/0114182 | A1 * | 5/2010 | Wilcox | A61B 17/7079 |
| | | | | 606/86 A |
| 2010/0130857 | A1 * | 5/2010 | Szinicz | A61B 17/02 |
| | | | | 600/235 |
| 2013/0245380 | A1 * | 9/2013 | Vogel | A61B 1/31 |
| | | | | 600/205 |
| 2014/0039266 | A1 * | 2/2014 | Porat | A61B 1/06 |
| | | | | 600/205 |
| 2018/0049626 | A1 * | 2/2018 | Slate | A61B 1/31 |
| 2018/0235444 | A1 * | 8/2018 | Tsai | A61B 1/303 |
| 2019/0247087 | A1 * | 8/2019 | Brown | A61B 17/0293 |

FOREIGN PATENT DOCUMENTS

| | | | | | |
|---|---|---|---|---|---|
| EP | 1598002 | A1 * | 11/2005 | | A61B 1/303 |
| EP | 2116178 | A1 | 11/2009 | | |
| EP | 2412302 | A1 | 2/2012 | | |
| EP | 2163211 | B1 | 11/2015 | | |
| EP | 3192449 | A1 | 7/2017 | | |
| GB | 2467573 | A | 8/2010 | | |
| WO | WO-2010076555 | A1 * | 7/2010 | | A61B 1/32 |

OTHER PUBLICATIONS

International Search Report and Written Opinion from corresponding International Application PCT/EP2022/052760 dated May 12, 2022, 10 pages.

* cited by examiner

PROCTOSCOPE

TECHNICAL FIELD

The present invention relates to a proctoscope.

TECHNICAL BACKGROUND

Up to 25% of the population older than 50 years are suffering from hemorrhoids. Hemorrhoids can be painful and cause severe problems for the affected persons.

There are several methods of treatment, all associated with varying degrees of complications. One of the most used modern techniques implies occlusion of supplying arteries to the anus with a ligature; thereafter the mucosa is lifted and secured in the lifted position by 4-5 stitches.

An alternative method is conducted by using the device for treatment of hemorrhoids disclosed in EP2163211. The disclosed device is intended for surgical stapling to generate the desired treatment of hemorrhoids by cutting away and staple the mucosa together again and thereby lifting the mucosa by 2-3 cm. The treatment is effective but is associated with severe complications like postoperative pain, sepsis and even death. The cost is high due to the necessity of anesthesia and the cost of the device.

The different known methods for treatment of hemorrhoids are all suffering from different drawbacks and there is consequently a need for improved technical solutions that makes it possible to reduce the surgery time, treatment cost and improve the outcome of the treatment.

SUMMARY OF THE INVENTION

The present invention relates to a proctoscope that makes it possible to at least some extent reduces the problems defined above.

The proctoscope comprises:

a body;

a handle extending from the body;

an elongated element comprising a forward end and an aft end, said aft end is attached to the body and open such that the interior of the elongated element is accessible via the aft end, said elongated element is extending along a longitudinal axis L, at least one opening formed in the elongated element between the forward and aft end, and/or a transparent section formed in the elongated element between the forward and aft end;

a reference marking arranged along the at least one opening and/or transparent section, said reference marking is readable via the open aft end of the of the elongated element, The proctoscope is characterized in that the proctoscope furthermore comprises a positioning device for supporting the proctoscope in the intended position relative a treatment area, said positioning device comprising:

an elongated position adjustment device with a forward end contact surface, said position adjustment device is movably arranged along an axis substantially parallel to axis L in the body and extending from the body in the same direction as the elongated element from the body, and locking means arranged to secure the elongated position adjustment device in a selected position, wherein the forward end contact surface is intended to bear against the skin of a patient to maintain and support the proctoscope in a position along the longitudinal axis is L where the treatment area is arranged in the intended position in relation to the reference marking.

In order to ensure the desired outcome of surgical treatment of hemorrhoids it is essential to establish the exact position of the areas that needs treatment. The proctoscope according to the invention is intended to be introduced in the rectum of the patient and facilitate the determination of the location of the treatment area within the rectum prior to the treatment of the hemorrhoids by surgery and maintain the proctoscope in the desired position during surgery.

The at least one opening and/or a transparent section makes it possible to detect the position of the prolapsed anal mucosa and positioning the proctoscope such that the prolapsed anal mucosa is arranged in the intended position relative the reference marking of the proctoscope. Once the position of the area that needs treatment is determined, the position of the proctoscope along axis L is adjusted such that the area that needs treatment is arranged in the intended position along the elongated element and the position adjustment device arranged in a position where the forward contact surface bears against the skin of the patient somewhere in the area around the rectum to support the and maintain the proctoscope in the desired position along axis L. Furthermore, the handle facilitates the introduction and angular positioning of the device. The elongated position adjustment device could be embodied in several different ways such as for example a screw or an elongated rod that could be secured in the desired position.

In one embodiment of the proctoscope, the reference marking is intended to be positioned adjacent to the intended treatment area or a reference position such as a linea dentata and the elongated position adjustment device locked in a position such that the end contact surface is bearing against the skin of the patient. The linea dentata is a very good reference position since the surgery preferably takes place well inside the linea dentata where there is a smaller risk that the surgical treatment will cause sever pain for the patient.

In one embodiment of the proctoscope, the at least one opening and/or transparent section is elongated and extending substantially parallel to axis L. The elongated opening and/or transparent section provides visible access to a larger section of the rectum which could facilitate determining the areas where treatment is needed.

In one embodiment of the proctoscope, the elongated element is made of a transparent material. This embodiment is favourable since the transparent elongated element will make it possible to visually inspect the entire area of the rectum surrounding the transparent elongated element.

One embodiment of the proctoscope further comprises means for illuminating the interior of the elongated element to facilitate the visibility during positioning of the proctoscope along axis L.

In one embodiment of the proctoscope, the reference marking extend along the at least one opening and/or transparent section substantially parallel to the axis L and is readable via the open aft end.

In one embodiment of the proctoscope, the forward contact surface is substantially flat and arranged substantially perpendicular to the elongated position adjustment device to provide a comfortable and reliably support against the skin of the patient.

In one embodiment of the proctoscope, the elongated position adjustment device is adjustable between an extended end position and an retracted end position.

In one embodiment of the proctoscope, the elongated position adjustment device is configured to be movable between a first angular position where the elongated position adjustment device is able to slide in the device body and a second angular position where the locking means are securing the elongated position adjustment device in the desired position.

In one embodiment of the proctoscope, the elongated position adjustment device and the locking means have a male/female configuration to lock the elongated position adjustment device in the desired position.

In one embodiment of the proctoscope, the elongated position adjustment device and the device body comprises corresponding treads such that the elongated position adjustment device is moved by turning the elongated position adjustment device and the locking means are embodied as a high friction material arranged on the treads so secure the elongated position adjustment device in the desired position.

In one embodiment of the proctoscope, the elongated element has an open forward end and the proctoscope furthermore comprises an elongated core member removably fitted within the elongated member. The elongated core element has a rounded forward end to facilitate introduction in the rectum of the patient.

In one embodiment of the proctoscope, the elongated element is removably fitted to the device body and replaceable by a proctoscope treatment element with a similar size and shape as the elongated element. This embodiment is favourable since the desired position for the proctoscope is determined with the elongated element fitted to the body and the elongated positioning device locked in the selected position. The proctoscope is extracted from the rectum and the elongated element replaced by the treatment element and easily inserted to the same position in the rectum since the positioning device will ensure that the proctoscope is arranged in the same position along axis L, i.e. the position where the forward contact surface is bearing against the skin of the patient.

During use of the proctoscope, the steps below are conducted:

Inserting the elongated element in the rectum of a patient to a position where the intended treatment area is arranged in the intended position relative the reference marking;

adjust the position of the elongated position adjustment device (7) to a position where the forward end contact surface (8) bear against the skin of the patient to maintain and support the proctoscope in the desired position;

secure the elongated position adjustment device (7) in the selected position by the locking means.

The proctoscope will be more accurate positioned during the entire surgery which will facilitate the surgery and improve the final result of the surgery.

Furthermore the additional steps below may be conducted:

extracting the elongated element from the rectum;

removing the elongated element from the body and fitting a proctoscope treatment element (20) with a similar size and shape as the elongated element to the body;

inserting the proctoscope treatment element in the rectum of the patient to the position where the forward end contact surface (8) bear against the skin of the patient to maintain and support the proctoscope in the desired position.

These additional steps are favourable since the positioning of the proctoscope can be done with the elongated element that provide visible access to the intended treatment area. When the proctoscope is in the intended position the positioning device is locked in the desired position and the proctoscope extracted from the rectum. The elongated element of the proctoscope is then replaced by the treatment element that will be used to conduct the surgery and inserted to the position where the forward end contact surface bear against the skin of the patient to maintain and support the proctoscope in the desired position. The possibilty to set the position with the elongated element that provides good visibility of the treatment area ensures a good result from the surgery and facilitates the process considerably.

In an alternative use of the proctoscope according to the invention, the elongated position adjustment device is provided with an indexing scale extending along the elongated position adjustment device. Instead of replacing the elongated element by the treatment element when the desired position of the support device, i.e. the elongated position adjustment device and the locking means, has been determined a reference value is determined from the indexing scale. The reference value is then used to calibrate the support device, i.e. the elongated position adjustment device and the locking means, of a corresponding substantially identical proctoctoscope used for conducting the surgery. This arrangement could be favourable to reduce the risk for contaminations since one proctoscope is used for inspection and determining the position of the treatment area while a separate, disinfected proctoscope is used for conducting the surgery. If a separate proctoscope is used for the surgery it is essential that the two proctoscopes have the same size and dimensions so the surgery is conducted in the intended treatment area.

BRIEF DESCRIPTION OF THE DRAWINGS

The above as well as further objectives, features and advantages with the present invention will become apparent when studying the following illustrative and non-limiting detailed disclosure of preferred embodiments of the present invention, with reference to the appended drawings.

All figures are schematic, not necessarily to scale, and generally only illustrating selected parts which are necessary to elucidate the invention, wherein other parts may be omitted or merely suggested.

DETAILED DESCRIPTION

The present invention, as previously stated, relates to proctoscope intended to facilitate the treatment of hemorrhoids.

The proctoscope comprises several different component that will be described in detail with reference to the attached figures.

Figure 1:
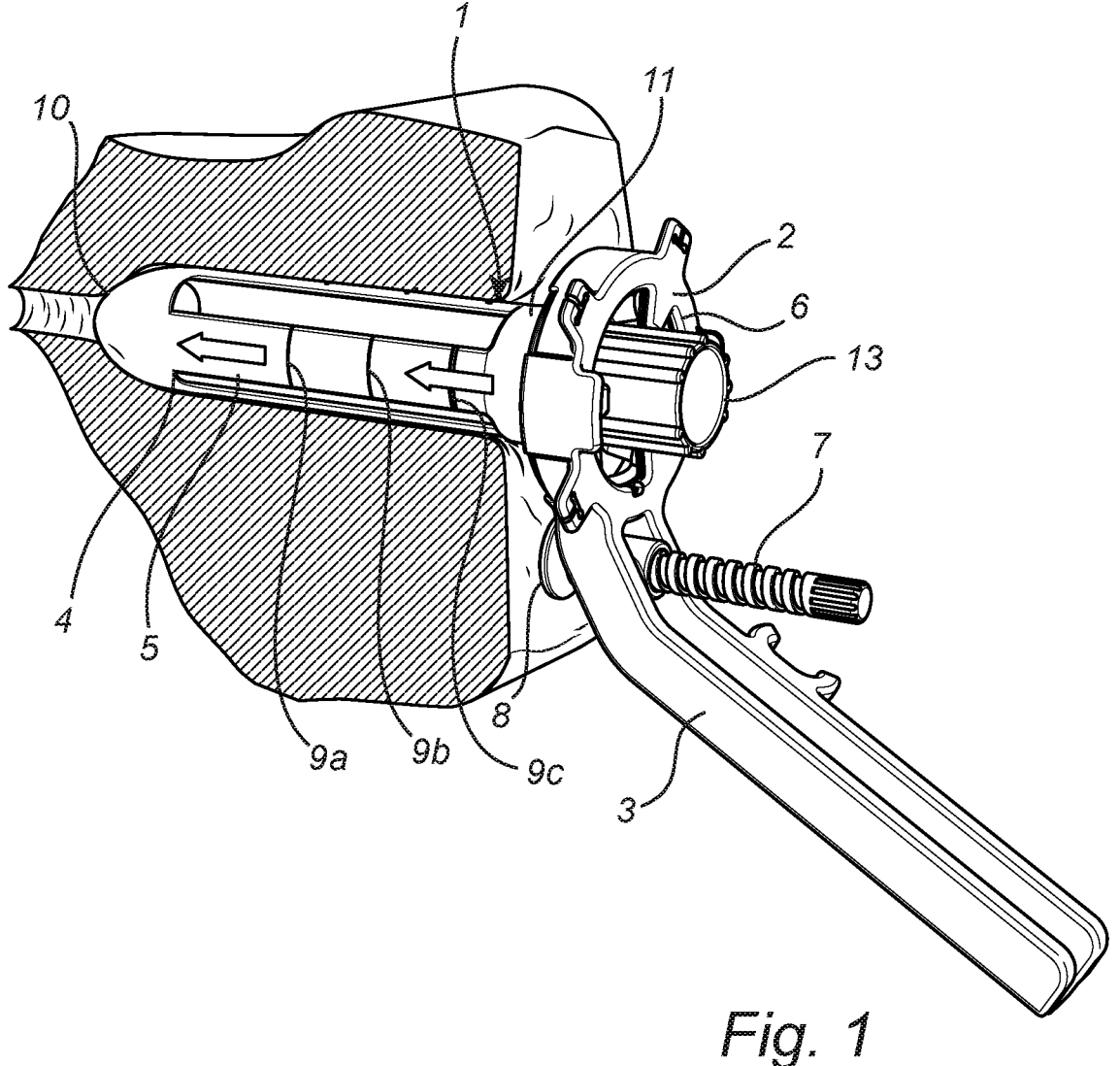
FIG. 1 illustrates a perspective view of a first embodiment of the proctoscope according to the invention.

A first embodiment of the proctoscope 1 according to the invention is illustrated in FIG. 1 and comprises a body 2 arranged to support the different components of the proctoscope 1. The body 2 is shaped as an annular member with a substantially circular passage 6 extending through the body 2. The circular passage 6 is arranged in a plane transverse to a longitudinal axis L of the proctoscope.

The proctoscope furthermore comprises a curved handle 3 extending in substantially radial direction from the longitudinal axis L from the body 2. The design of the handle could however be modified in different ways to adapt the proctoscope to patients of different sizes/dimensions. The handle is intended to facilitate the operation of the proctoscope.

One essential part of the proctoscope is an elongated element 4 extending from the body 2 along the longitudinal axis L. The elongated element 4 comprises a forward rounded end 10 and an aft end 11 removably attached to the body. The aft end is open such that the interior of the elongated element is accessible via the aft end and the passage in the body. The elongated element 5 has a substantially circular cross sectional shape with substantially the same radius along the entire elongated element. At least one opening 5 is formed in the elongated element between the forward and aft end and/or a transparent section is formed in the elongated element between the forward and aft end to make it possible to visually inspect the anal mucosa and hemorrhoids via the open aft end of the elongated member and the passage formed in the body when the elongated element is arranged in the rectum of the patient. In an alternative embodiment, the entire elongated element is made of transparent material to further improve the possibility to the visually inspect the tissue. This embodiment could also be used in combination with at least one opening in the elongated element.

The elongated element is provided with a reference marking 9a, 9b, 9c arranged along the at least one opening and/or transparent section. The reference marking could for example be one or more lines, or a scale arranged along the at least one opening, or in the transparent section, such that the reference marking is readable via the open aft end of the of the elongated element.

The proctoscope furthermore comprises a positioning device for supporting the proctoscope (1, 1') in the intended position relative the identified treatment area. The embodiment of the positioning device illustrated in FIG. 1-8 comprises an elongated position adjustment device 7 extending from the body substantially parallel to the elongated element 4 in the same direction as the elongated element 4, i.e. parallel to axis L. The elongated position adjustment device in the illustrated embodiment is designed as a screw. The screw has an external thread and is arranged in a corresponding hole with an internal tread in the device body 2 such that the position along axis L is adjusted between a forward position and an aft position by turning the screw. The position adjustment device comprises a forward substantially flat forward end contact surface 8 arranged substantially perpendicular to the longitudinal axis L. The flat forward en contact surface 8 is intended to bear against the skin of the patient in the area surrounding the rectum of the patient. The positioning device furthermore comprises locking means arranged to secure the elongated position adjustment device in the selected position. In this embodiment the locking means are embodied as surface structure or layer of high friction material on the respective tread to maintain the elongated position adjustment device, i.e. screw, in the desired position.

Figure 9:
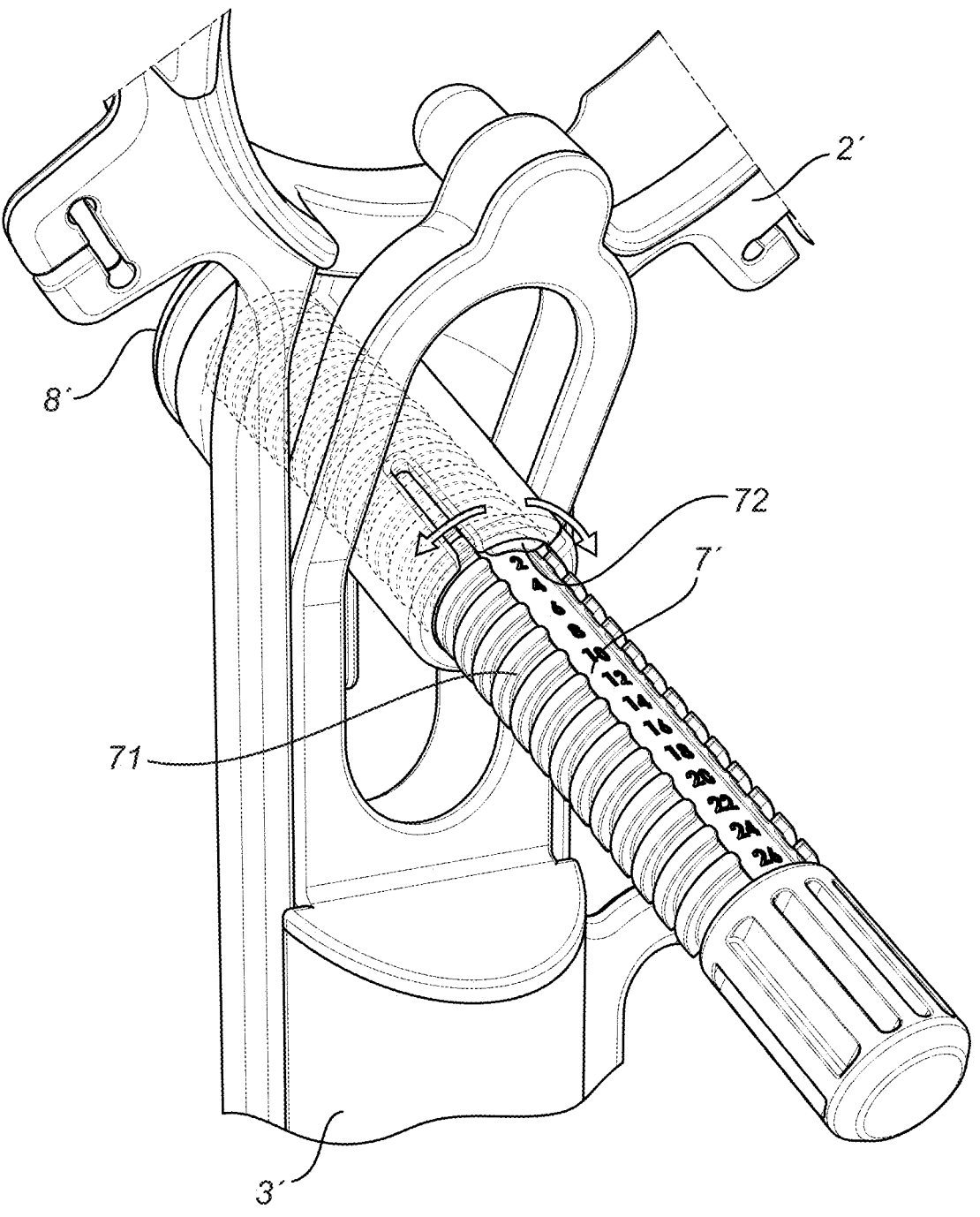
FIG. 9 illustrates a second embodiment of the positioning device.

An alternative embodiments of the positioning device is illustrated in FIG. 9. In this embodiment the elongated position adjustment device 7' is embodied as an elongated rod slidably arranged in a corresponding passage in the body 2'. The elongated rod is turnable, illustrated by arrows in FIG. 9, around its longitudinal axis between a first angular position where the elongated position adjustment device is able to slide in the device body 2', and a second angular position where the locking means 71, 72 are securing the elongated position adjustment device in the desired axial position. The locking means have a male/female configuration with notches 71 arranged along the elongated position adjustment device 7' and a corresponding locking element 72 arranged in the body 2'.

Furthermore, the elongated position adjustment device is provided with an indexing scale extending along the elongated position adjustment device 7'. The indexing scale makes it possible to determine a reference value representative for the desired position of the proctoscope.

A further alternative is to provide the aft end of the elongated position adjustment device with an elastic member that could be bent outwards from the longitudinal direction and locked in for example a clamp such that the elongated position adjustment device is locked in the desired position.

Before surgical treatment of the hemorrhoids is initiated, the proctoscope 1 according to the invention, i.e. the elongated element 4, is arranged in the rectum of the patient. The elongated position adjustment device is adjusted along axis L such that the elongated element is maintained in the position along axis is L where the hemorrhoids are positioned in the intended position along the elongated element 4. Once the elongated position adjustment device is locked in the desired position to maintain the proctoscope in the desired position along axis L, the proctoscope could be extracted from rectum and easily returned to the desired set position since the positioning device will ensure that the proctoscope will be returned to the determined desired position. The positioning device prevents that the elongated element is introduced to long in forward direction, into rectum of the patient.

The reference markings on the proctoscope could be embodied in different ways but in one favourable embodiment one reference marking, illustrated in the figures by reference numeral 9c, is intended to be positioned in line with the linea dentata in the rectum of the patient. The position of this reference marking, i.e. reference 9c, further aft along the elongated element ensures that when the reference marking 9c is aligned with the linea dentata, the treatment area is positioned inside the rectum where humans have limited sensation for pain.

In order to further improve the visibility, the positioning device could comprise means for illuminating the interior of the elongated element. The means for illuminating the interior could have different configurations but preferably comprises one or more diodes or lamps arranged in the body such that the interior of the elongated element in enlightened. The one or more diodes or lamps are powered either by batteries arranged in the body, or by an external power source, i.e. electrical power, connected to the body. A further alternative is to use an external light source and direct the light to the desired position by optical fibres.

Figure 2:
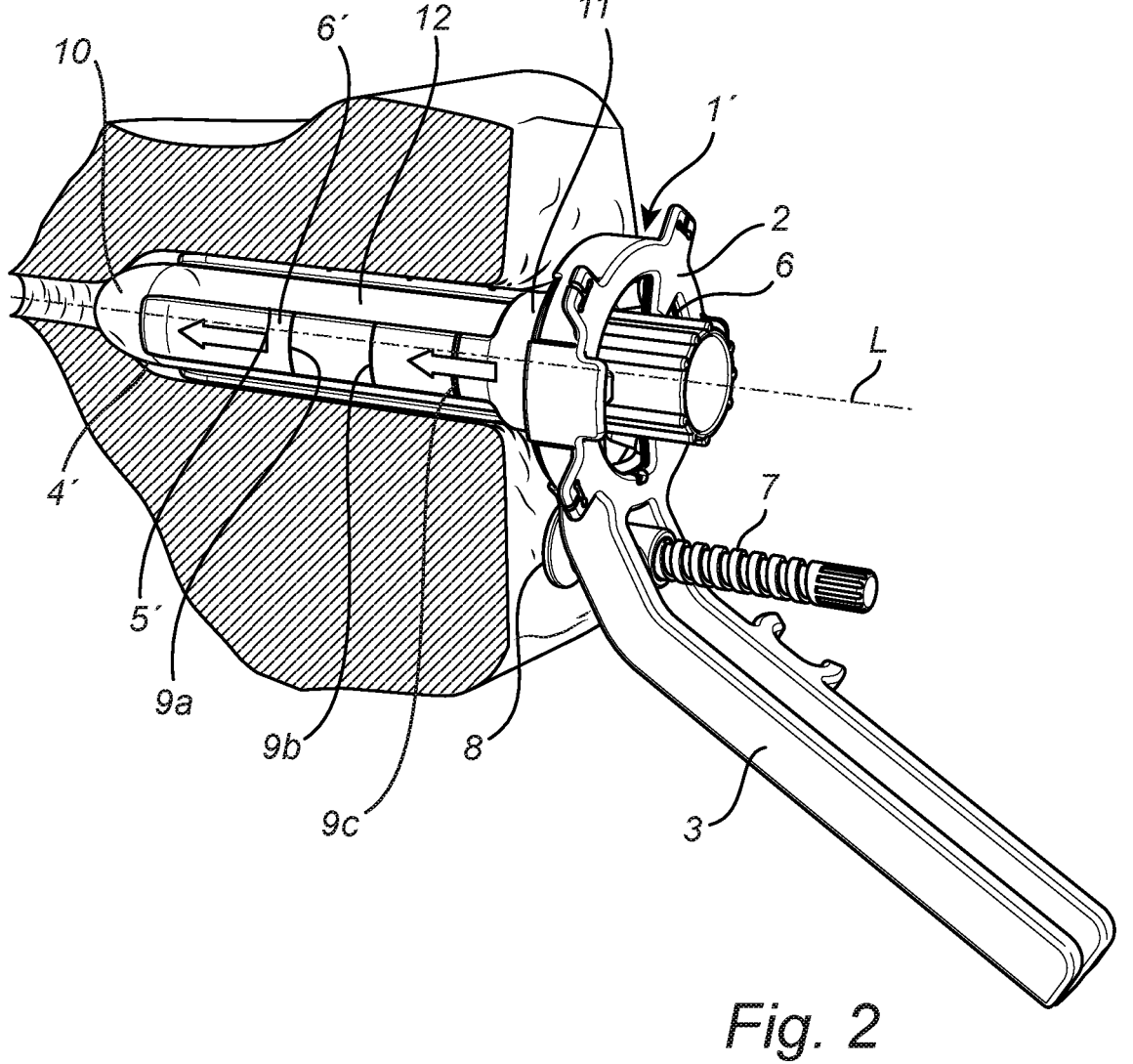
FIG. 2 illustrates a perspective view of a second embodiment of the proctoscope according to the invention.
Figure 3:
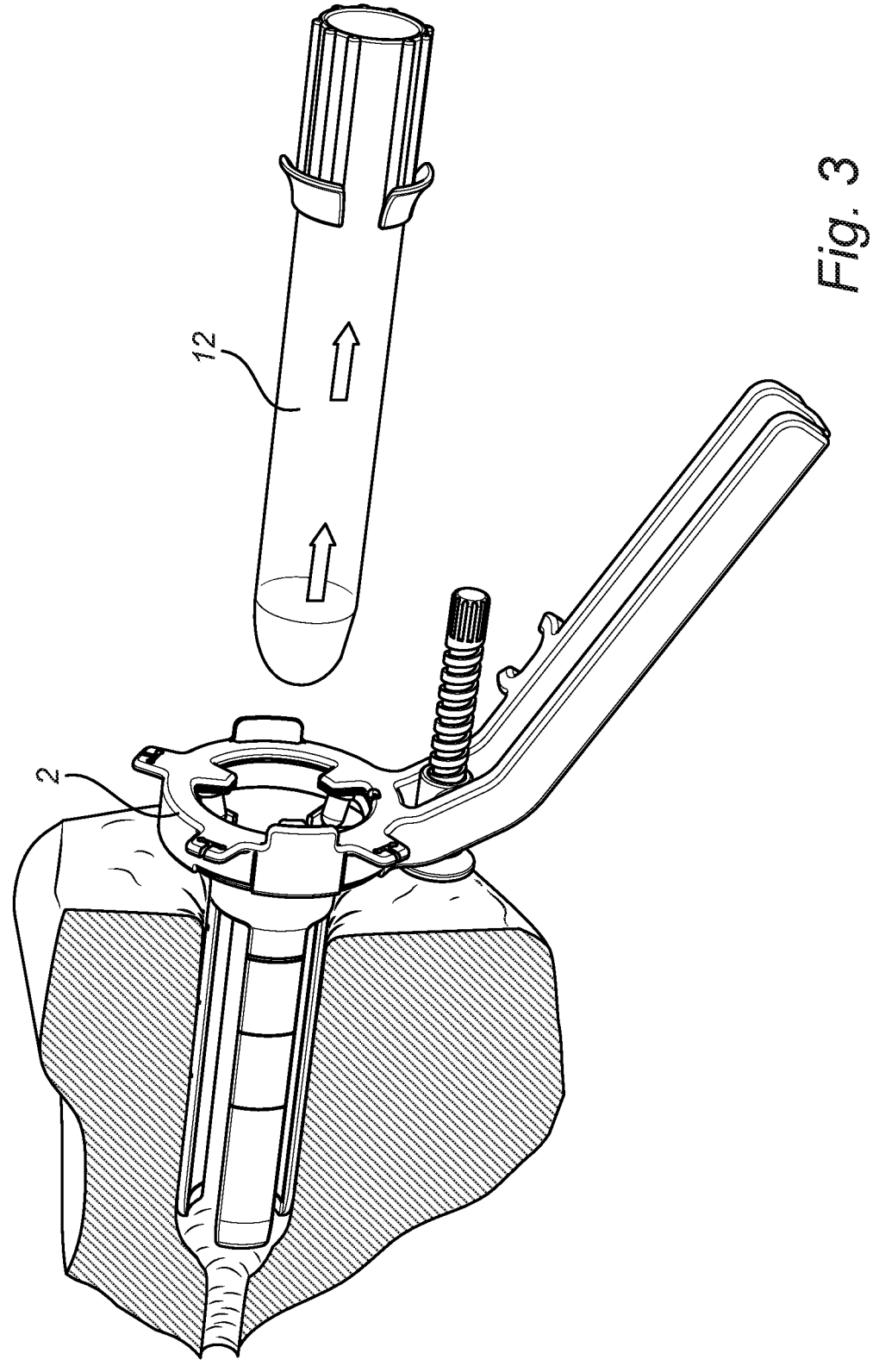
FIG. 3 illustrates a perspective view of the proctoscope in FIG. 2.
Figures 4, 5:
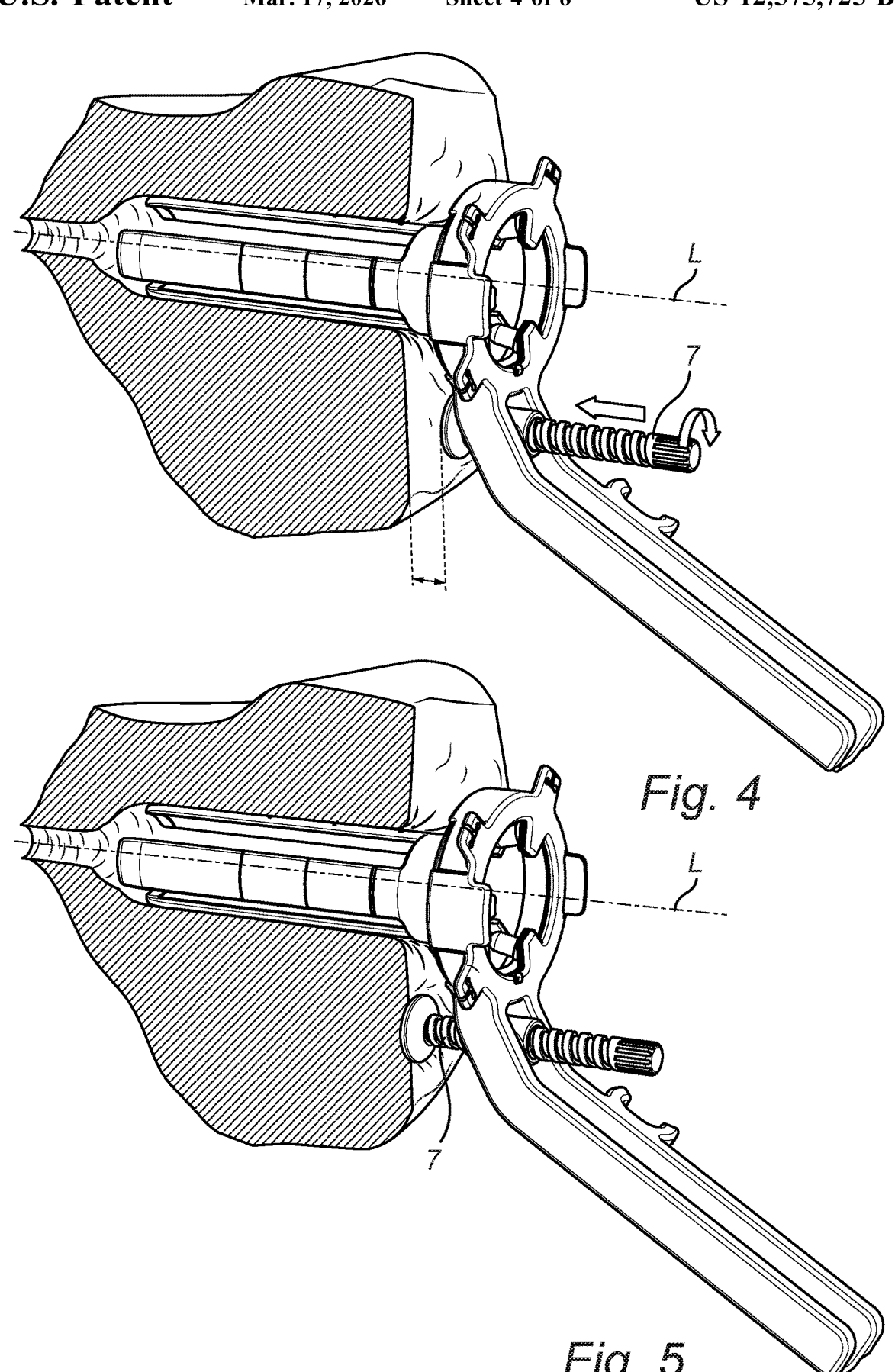
FIG. 4 illustrates a perspective view of the proctoscope with the position adjustment device in a first configuration.
FIG. 5 illustrates perspective view of the proctoscope with the position adjustment device in a second configuration.

A second embodiment of the proctoscope 1' is illustrated in two different configurations in FIGS. 2 and 3. In this embodiment the body 2 is substantially the same as in the previous embodiment but the elongated element 4' is shaped like a tube with an open forward end 10. In this embodiment the at least one opening is formed as an elongated slot 5' extending from the aft end 11 all the way to the open forward end. The proctoscope furthermore comprises an elongated core member 12 removably fitted within the tube shaped elongated member to close the at least one opening 5'. The core member 12 has a length corresponding to the length of the elongated element such that the rounded forward end of the core member provides an rounded forward end of the elongated element and closes the forward end.

Once the proctoscope is introduced in the rectum of the patient, the core member 12 is removed via the open aft end of the elongated element and the passage in the body to open the at least one opening 5' and improve the visibility. This embodiment is favourable since the introduction of the elongated element in the patient is facilitated since the at least one opening is closes by a smooth surface. This embodiment is particularly advantageous when the at least one opening has a considerable size.

Also in this embodiment a transparent section could be formed in the elongated element, or the entire elongated element made of a transparent material to further facilitate the visually inspection the anal mucosa and hemorrhoids.

In both embodiments of the proctoscope the elongated element is preferably removably fitted to the body. When the linea dentata is aligned with the reference marking and the elongated position adjustment device 7 arranged in the desired position along the longitudinal axis, the proctoscope is removed from the rectum and the elongated element replaced by a treatment element 20. The treatment element comprises a tube shaped element 21 designed to be fitted to the body 2 at the same position as the elongated element and has substantially the same size and dimensions as the elongated element. In the illustrated embodiment the aft end of the tube shaped element is flared outwards to form a connection socket 2' intended to be fitted to the body.

The treatment element 20 is intended for treatment of hemorrhoids and comprises an anal mucosa support device 22, 22a, 22b, 22c removably arranged within the tube-shape element 21 such that said support device is exposed in an opening 23 in the tube shaped element. The treatment element could also be designed with two, or more, similar openings arranged around the periphery of the tube-shaped element and one anal mucosa support device is then arranged in each opening.

The elongated tube-shaped element 21 constitutes the outer casing of the treatment element 20. The tube shaped element 21 comprising a rounded forward end 24 that is intended to be arranged in the rectum of the patient. The tube shaped element 21 further comprises an open aft end 25 intended to be arranged in the central open passage in the body 2 such that the interior of the tube-shaped element is accessible via the passage in the body 2. The tube-shaped element 21 is substantially straight and extending along the longitudinal axis L. The tube-shaped element could be made in different lengths and the cross sectional shape of the tube-shaped element transverse to axis L is substantially circular in order to facilitate the insertion of the device when the treatment is initiated. Alternative cross sectional shapes could also be oval, triangular, rectangular, pentagonal or hexagonal etc with rounded corners. The tube shaped element is preferably made of a plastic material.

The angular position of the opening 23 in the tube-shaped element around axis L corresponds to the angular position of the at least one opening in the elongate element when the elongated element and treatment element are fitted to the device body in the correct position.

The illustrated embodiment of the anal mucosa support device 22 comprises a first 22a, an intermediate 22b and a second 22c elongated part arranged to extend substantially parallel to axis L. The first, intermediate and second elongated part are arranged adjacent to each other and are removably arranged within the tube shape element.

The anal mucosa support device comprises at least two cavities 26 for the anal mucosa arranged at the same position along the longitudinal axis L as the intended treatment area corresponding to the position of the reference marking of the elongated element such that the position defined by the positioning device ensure that the identified treatment area will be correctly positioned when the treatment element is inserted to start the surgery.

The treatment area, and consequently also the two cavities 26, is preferably arranged such that there is a distance within the range of 10 to 15 mm along axis L between the linea dentata and outer end of the treatment area, i.e. the edge of the cavity arranged closes to linea dentata.

The treatment element will end up in the intended desired position when entered in the rectum of the patient to the position where the forward end contact surface bear against the skin of the patient.

The cavities 26 are arranged along the longitudinal axis L substantially in the centre of the opening 23 in the tube shaped element. Each cavity 26 has an open side facing the opening 23 in the tube shaped element such that the anal mucosa can enter each of the cavities.

The first 22a, intermediate 22b and second 22c elongated part are designed to be arranged adjacent to each other substantially in the centre of the opening 23 and each of the cavities 26 are arranged along the contact surfaces between the first 22a, the intermediate 22b and the second 22c elongated part such that the cavities are formed by cavities in the first, the intermediate and the adjacent second elongated part, i.e. the cavity is formed by the three elongated parts. Furthermore, needle passages 27 are formed along the contact surface between the first and the intermediate part, and between the intermediate and the second part. The illustrated embodiment of the proctoscope comprises four needle passages 27, i.e. one needle passage 27 between each of the cavities 26 in the anal mucosa support device 22. The needle passages 27 are opened when the first, the intermediate and the second elongated part are separated from each other to release a needle 50, or a suture thread, a staple or securing means extending through the needle passage 27.

The needle passages 27 constitutes the needle guide structure formed in the elongated tube-shaped element and the anal mucosa support device such that a needle 50 is guided during movement within the tube shaped element from an extracted position in which the needle is arranged outside the opening 23 in the elongated tube-shaped element 21 through the cavities 26 in the anal mucosa support device 22 to a position where the needle 50 extend across the opening 23 in the tube-shaped element. Each needle passage 27 has a size and shape corresponding to the cross sectional dimension and shape of the needle 50 such that the needle is able to easily pass through each needle passage 27 when the needle is moved from the retracted to the extracted position. Preferably the side of the needle passage that is facing the aft end of the device is slightly widened to guide the needle into the centre of the needle passage. In the illustrated embodiment, two needles are formed as one single element by a connecting structure 52 in the aft end of the needles such that the two needles 50 are moved simultaneously in the adjacent needle passages. The connecting structure is preferably slightly elastic such that the needles also could be moved independently from each other.

Each cavity 26 in the anal mucosa support device 20 comprises a bottom structure and the distance in radial direction from axis L between the centre of the needle passage and the bottom structure is between 2 and 12 mm. In order to ensure that the anal mucosa is correctly arranged in the cavities 26 in the anal mucosa support device, the bottom structure of each cavity comprises at least one opening in each cavity, said openings are connected to some sort of means that is able to provide a pressure below the surrounding pressure, such as for example a manual or electrically powered pump or an externally arranged source of sucking action, such that the anal mucosa is sucked into the cavities 26.

The anal mucosa support device 22 is removably arranged within the tube shaped element 21 and maintained in the intended position within the tube-shaped element by a removable locking element. The locking element is shaped like an elongated plate with a length, along axis L, and width corresponding to the interior dimensions of the elongated tube shaped element. The positioning and securing of the locking element within the tube shaped element is provided by guiding rails 32 arranged along the inner peripheral wall of the tube shaped element on each side of the opening in the tube shaped element such that the locking element could slide parallel to the longitudinal axis L. The first, intermediate and second elongated element of the anal mucosa support are fitted within a recess on the side of the locking element that is facing the opening 23 in the tube shaped element such that the first, intermediate and second element are maintained in the intended position. The locking element is arranged within the tube shaped element to force the anal mucosa support device into the intended position and maintain the anal mucosa support device in the intended position with the cavities exposed in the opening of the tube-shaped element.

In the above description of the treatment element 20 only one arrangement comprising one opening 23 in the tube-shaped element 21, one anal mucosa support device 22 and one locking element 30 has been described but preferably the treatment element 20 is designed to comprise two, alternatively three or up to six similar, corresponding substantially identical arrangements.

The treatment element 20 is introduced in the rectum of the patient in order to make it possible for a surgeon to treat the hemorrhoids by surgery. Once the proctoscope is in the intended position, the prolapsed anal mucosa is arranged in the cavities 26 in the anal mucosa support device. The needle guide structure 27, formed in the elongated tube-shaped element and the anal mucosa support device, provides guidance for the needle, or needles, 50 during movement within the tube shaped element 21 from the extracted starting position, through the cavities 26, i.e. through the anal mucosa arranged within the cavities, to the position where the needle 50 extend across the entire opening 23 in the tube-shaped element 21 and through the anal mucosa arranged in the different cavities 26 such that folds are generated in the anal mucosa.

The needle 50 is used to introduce a suture thread, a staple or securing means through the different folds of the anal mucosa. Different alternatives to enter the suture thread, the staple or securing means could be used.

Either the suture thread, staple or securing means is introduced together with the needle, or the needle is first moved from the retracted position to the extracted position where the needle tip is secured in a corresponding docking element in the end of a suture thread, a staple or securing means arranged within the forward end of the treatment element. The suture thread, the staple or securing means is introduced in the anal mucosa at the same time as the needle 50 is retracted from the extracted position and the suture thread, the staple or securing means are drawn through the anal mucosa.

As soon as the suture thread, staple or securing means is correctly positioned, the removable locking element is removed and the anal mucosa support device 22a, 22b, 22c released from the locked position such that they can be removed from the opening 23 via the open aft end 25 to free the anal mucosa and the suture thread, staple or securing means from the treatment element. This is essential to make it possible to remove the treatment element from the rectum after the suture thread, staple or securing means are arranged extending though the anal mucosa to allow the desired tightening of the suture thread, staple or securing means and permanently secure the anal mucosa in the lifted position.

The treatment element facilitates the surgical treatment since the needle guide structure and the anal mucosa support device ensures that the needle 50, and in the end the suture thread, staple or securing means, is extending through the intended area of the anal mucosa arranged in each of the cavities 26 which ensures that the desired result is achieved.

In the case of severe hemorrhoid problems, the rectum mucosa needs to be lifted more. The distance between the reference markings could be extended and the number of cavities in the anal mucosa support device increased accordingly such that further folds on the anal mucosa are created, which results in that the lifting effect is increased considerably.

The treatment element 20 furthermore comprises one closing element 40 for each opening 23 in the tube shaped element 21. The closing element 40 has a shape corresponding to the cross sectional shape of the tube-shaped element to provide a smooth outside shape of the treatment element and a length corresponding to the length of the opening 23 to completely close the opening when arranged in the device. The closing element is removably arranged in the tube-shaped element and intended to close the opening in the tube shaped element to facilitate insertion of the device in the rectum of the patient. When the device is in the desired position in the rectum, the closing element that is extending all the way to the aft end is removed via the aft end of the tube shaped element to expose the opening in the tube shaped element and make it possible for the anal mucosa to enter the cavities. The closing element 40 is arranged to slide in substantially straight recesses formed along the elongated sides of the opening in the tube shaped element substantially parallel to the longitudinal axis L.

When the proctoscope is fitted in the intended position in the rectum of the patient and the closing element are removed, the open aft end of the tube shaped element 12 is closed by a sealing plug 54. The sealing plug 54 is schematically illustrated but is designed to close and seal the open aft end and the passage in the device body 2 such that pumping or suction means could be connected to the interior of the tube shaped element 21 via a connection in said sealing plug 54. The sealing plug could also be provided with an elastic tube extending from the plug to facilitate the connection to the pumping or suction means. Alternative embodiments to provide the desired connection of pumping or suction means to the interior of the tube shaped elements are also possible. For example, the pumping or suction means could be connected to the interior of the proctoscope via a connection arranged on the device body 2 or the handle 3 and a channel integrated in the device and connected to the interior of the tube-shaped elements 21. When the pumping or suction means, not illustrated, are activated the pressure within the tube shaped element 21 is reduced and the anal mucosa is sucked into the cavities.

Once the anal mucosa is in the desired position within the cavities 26 the needle 50 is pushed from the retracted position through the needle passages 27, across the cavities 26 and the anal mucosa arranged in the cavities all the way to the opposite side of the opening 23 in the tube shaped element 21.

In order to ensure that the anal mucosa is arranged in the cavities as intended the open aft end 25 is sealed by the plug 54 with a shape and dimension corresponding to the open aft end. In one favourable embodiment of the plug 54 an elastic membrane 55 is arranged to close an opening in the plug. The elastic membrane 55 is visible from the outside of the device such that the surgeon, or operator, is able to monitor that the desired reduced pressure within the treatment element is established and the anal mucosa sucked into the cavities correctly. The elastic membrane could also be transparent to make it possible to see the interior of the proctoscope once the plug is arranged to close the open aft end 25. Other embodiments are also possible to visually sign that the desired low pressure is reached within the proctoscope such as a small button resiliently supported in the device and when the desired low pressure is achieved the force from the spring is exceeded by the low pressure and the button retracted from its starting position.

Different types of suture wires, stamps or securing arrangement could be used in combination with the proctoscope and when the needle and suture thread, staple or securing means is arranged extending through the anal mucosa the needle is removed and the suture thread, staple or securing means tightened and permanently secured such that the desired lift of the prolapsed anal mucosa is achieved.

The treatment element could be configured for use in combination with different alternatives to secure the anal mucosa in the lifted position. For example, within the forward end of the device tube-shaped element, a suture thread could be arranged inside the tube-shaped element before the treatment is initiated. In one end of the suture tread a forward stop element is permanently secured and in the opposite end of the suture thread docking means, for example a loop or male/female fitting, are arranged. The docking means are positioned in the intended forward position of the needle tip. When the treatment element 20 is in the desired position within the rectum of the patient, the needle 50 is moved from the retracted position through the cavities to the docking means where the needle tip connects to the docking means such that the needle is connected to the docking means. The needle is then retracted together with the suture thread to a position where the forward stop element rest against the forward fold of the anal mucosa. The needle 50, the sealing plug 54, the locking element and the anal mucosa support device 20 are removed to free the tread and the anal mucosa from the anal mucosa support device. In order to achieve the desired lift of the anal mucosa an aft stop element is pushed forwards along the thread to force the anal mucosa folds towards the forward stop element. The aft stop element and the suture tread are either provided with a corresponding securing structure that prevents the rear stop element from moving backwards along the thread or permanently secured in the desired position by for example a knot. The aft stop element is arranged on the thread once the needle and needle sleeve are removed from the tread.

A very simple and reliable embodiment based on this general idea involves an elongated suture thread arranged within the treatment element before the surgery is initiated. One end of the suture thread comprises a docking element arranged in the position of the needle tip in the forward end of the opening 23. Once the needle is introduced the needle tip is connected to the docking element and the thread introduced through the anal mucosa when the needle is retracted. The length of the suture thread is at least long enough to ensure that the both ends of the suture thread extend all the way out through the open end of the device such that the surgeon can secure the ends of the thread by one or more knots and lift the anal mucosa.

Figure 6:
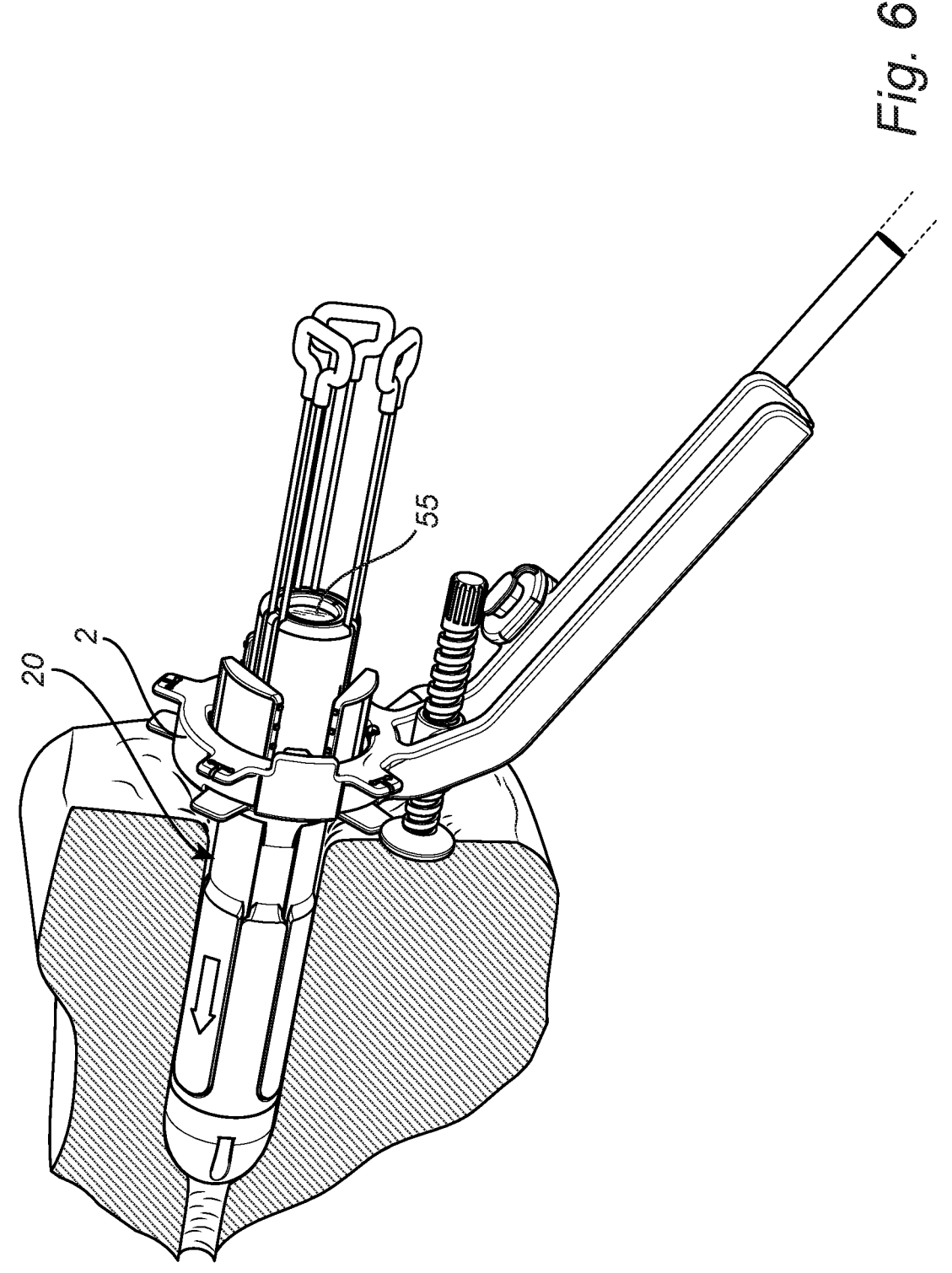
FIG. 6 illustrates another configuration of the proctoscope in perspective.
Figure 7:
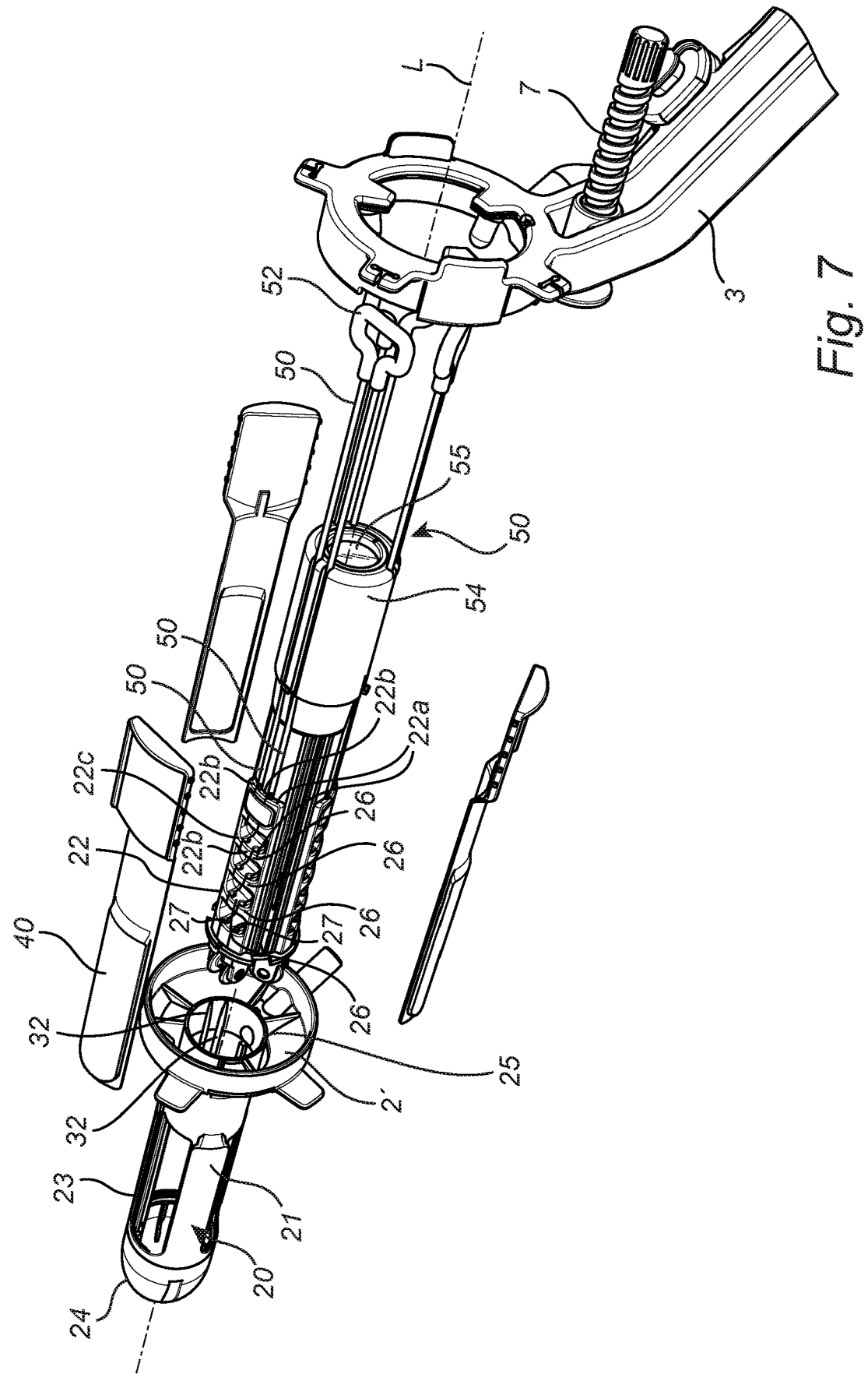
FIG. 7 illustrates a schematic exploded view of selected components of the proctoscope.
Figure 8:
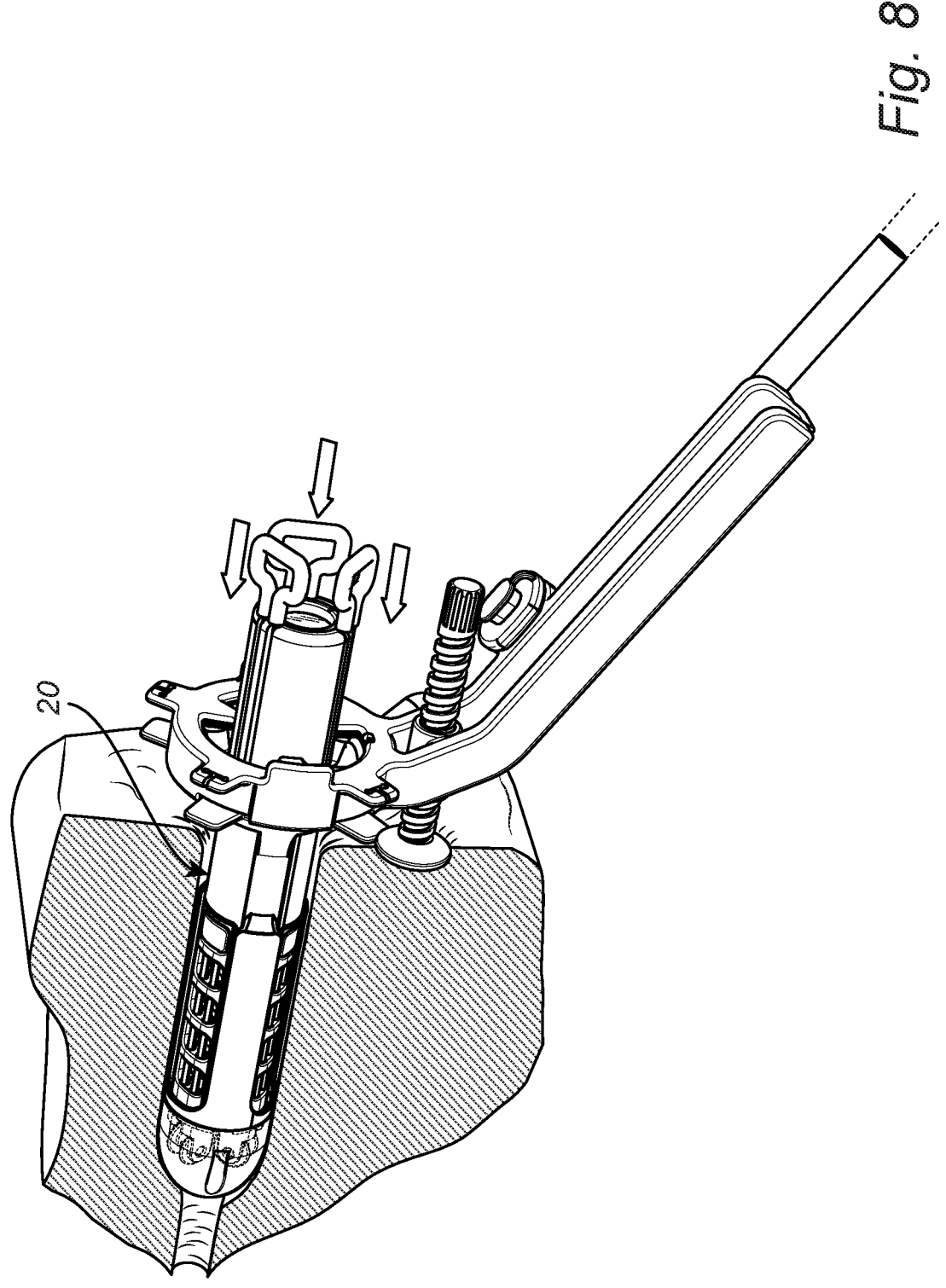
FIG. 8 illustrates selected parts of the proctoscope in FIG. 6 after introduction of the needles.

This embodiment is also very favorable in combination with an embodiment of the proctoscope comprising two parallel needles 50, illustrated for example in FIG. 6, since one single suture thread could be arranged in the forward end of the device with one end provided with docking means positioned in the forward end of one needle, and the second end of the suture thread provided with similar docking means positioned in the forward end of the other needle. Once the two needles have docked to the corresponding docking means, both ends of the suture thread are retracted through the folds of the anal mucosa such that both ends are extending out of the aft end of the proctoscope. After the suture threads have been tightened and the desired lift of the anal mucosa is achieved the two ends could be secured by one, or more, reliable knots.

While the invention has been illustrated and described in detail in the drawings and foregoing description, such illustration and description are to be considered illustrative or exemplary and not restrictive; the invention is not limited to the disclosed embodiments. The skilled person understands that many modifications, variations and alterations are conceivable within the scope as defined in the appended claims.

Additionally, variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope of the claims.

The invention claimed is:

1. A proctoscope comprising:
   a body;
   a handle extending from the body;
   an elongated element comprising a forward end and an aft end, said aft end is attached to the body and open such that the interior of the elongated element is accessible via the aft end, said elongated element is extending along a longitudinal axis L,
   at least one opening formed in the elongated element between the forward and aft end, and/or a transparent section formed in the elongated element between the forward and aft end;
   a reference marking arranged along the at least one opening and/or transparent section, said reference marking is readable via the open aft end of the of the elongated element, characterized in that the proctoscope furthermore comprises a positioning device for maintaining and supporting the proctoscope in an intended position relative a treatment area, said positioning device comprising:

an elongated position adjustment device with a forward end contact surface, said position adjustment device is movably arranged via engagement, for movement relative to the body and the elongated element, along an axis substantially parallel to axis L in the body and extending from the handle in the same direction as the elongated element from the body, and locking means arranged to secure the elongated position adjustment device in a selected position, wherein the forward end contact surface is intended to bear against the skin of a patient to maintain and support the elongated element at an inserted location along the longitudinal axis L associated with the with proctoscope being in the intended position and the treatment area being arranged in relation to the reference marking, and wherein the elongated position adjustment device is adjustable between an extended end position and a retracted end position, and the elongated position adjustment device is configured to be movable between a first angular position where the elongated position adjustment device is able to slide in the device body and a second angular position where the locking means is securing the elongated position adjustment device in the desired position.

2. Proctoscope according to claim 1, characterized in that the reference marking is intended to be positioned adjacent to the intended treatment area or a reference position, and the elongated position adjustment device locked in a position such that the end contact surface is bearing against the skin of the patient.

3. Proctoscope according to claim 1, characterized in that the at least one opening and/or transparent section is elongated and extending substantially parallel to axis L.

4. Proctoscope according to claim 1, characterized in that the elongated element is made of a transparent material.

5. Proctoscope according to claim 1, characterized in that it further comprises means for illuminating the interior of the elongated element.

6. Proctoscope according to claim 1, characterized in that the reference marking extend along the at least one opening and/or transparent section substantially parallel to the longitudinal axis L and is readable via the open aft end of the elongated element.

7. Proctoscope according to claim 1, characterized in that the end contact surface is substantially flat and arranged substantially perpendicular to the longitudinal axis of said elongated position adjustment device, said end contact surface is intended to bear against the skin of the patient.

8. Proctoscope according to claim 1, characterized in that the elongated position adjustment device and the locking means have a male/female configuration to lock the elongated position adjustment device in the desired position.

9. Proctoscope according to claim 1, characterized in that the elongated element has an open forward end and the device furthermore comprises an elongated core member removably fitted within the elongated member.

10. Proctoscope according to claim 1, characterized in that the elongated element is removably fitted to the body and replaceable by a proctoscope treatment element with a similar size and shape as the elongated element.

* * * * *